United States Patent [19]

Clarke et al.

[11] 4,031,852

[45] June 28, 1977

[54] MICROSCOPE SLIDE CENTRIFUGE

[75] Inventors: Louis W. Clarke, Raleigh, N.C.; Burton H. Sage, Jr., Medfield, Mass.

[73] Assignee: Corning Glass Works, Corning, N.Y.

[22] Filed: Jan. 2, 1976

[21] Appl. No.: 645,948

[52] U.S. Cl. .................................................. 118/52
[51] Int. Cl.² ........................................... B05C 11/08
[58] Field of Search .......................... 118/52–56; 34/8, 58; 427/240, 2, 346

[56] References Cited

UNITED STATES PATENTS

| | | | |
|---|---|---|---|
| 2,632,725 | 3/1953 | Marks et al. | 427/240 X |
| 3,705,048 | 12/1972 | Staunton | 118/52 X |
| 3,870,014 | 3/1975 | Buck | 118/52 |

FOREIGN PATENTS OR APPLICATIONS 665,366  5/1929  France .............................. 118/52

OTHER PUBLICATIONS

IBM Technical Disclosure Bulletin "Rheology Control of Films Deposited by Spin Coating Techniques" Esch et al., vol. 16, No. 6 (Nov. 1973) pp. 1730, 1731.
IBM Technical Disclosure Bulletin "Controlled Gap Photoresist Spinning Process" Holihan, Sr. et al., vol. 17, No. 11 [April 1975] p. 3281.

*Primary Examiner*—Morris Kaplan
*Attorney, Agent, or Firm*—Walter S. Zebrowski; Clarence R. Patty, Jr.

[57] ABSTRACT

A microscope slide centrifuge for spinning a slide in preparation of blood films for microscopic examination is disclosed. The centrifuge includes a platen suitable for accepting a microscope slide for spinning the slide with a flat surface thereof perpendicular to the spin axis of the centrifuge. An enclosure closely surrounding the platen is disposed adjacent the flat surface of the microscope slide and parallel therewith. The enclosure is firmly attached to the centrifuge platen and is spinnable therewith.

3 Claims, 5 Drawing Figures

MICROSCOPE SLIDE CENTRIFUGE

BACKGROUND OF THE INVENTION

This invention relates to an apparatus for preparing a blood smeared microscope slide for analysis and more particularly to spinning the microscope slide so as to produce the highest quality blood smear.

In the analysis of blood samples, the blood is smeared on a laboratory slide and the smear is stained. By counting the leukocytes on the stained smear, laboratory technicians performed what is referred to as a white blood cell differential. Automation of this differential has significant economic impact because the differential is performed very frequently at every hospital. A thesis by J. W. Bacus, "An Automated Classification of the Peripheral Blood Leukocytes by Means of Digital Image Processing", University of Illinois, Chicago, 1971, describes one automated system.

U.S. Pat. No. 3,883,852 issued to Douglas A. Cotter entitled "Image Scanning Converter for Automated Slide Analysis" describes a system developed by my co-workers for automatically scanning and determining the relative number of different types of leukocytes on a stained smear.

Centrifugally spinning a blood wetted slide to produce a monolayer blood film is described in a paper by M. Ingram and F. M. Minter, entitled "Semi-Automatic Preparation of Cover Glass Blood Smears Using a Centrifugal Device", Amer. J. Clin. Path. 51: 214–221, 1969. The method described in this paper includes flooding a cover glass with a layer of blood and centrifuging the cover glass rapidly in a plane parallel to the plane of rotation of the centrifuge. Excess blood is spun off leaving a monolayer of well spread blood cells on the cover glass. Centrifuges for spinning blood smear slides are commercially available. Such devices are available from: Plat General Corporation, (sold by PEI, Incorporated, Abington, Pa.); Perkin-Elmer Corporation, Wilton, Conn.; and Shandon Scientific Company Incorporated, Sewickley, Pa.

In using some of the commercially available centrifuges and blood spinning techniques described above, it has been found that the separation of the red cells was not the same for all blood samples. For some bloods the spinning resulted in blood films with sparsely populated areas interspersed with clumps of cells. For other bloods the technique produced a slide with overlapping cells. As mentioned in the article by Ingram, the morphology of the red cells was often altered. The cells appeared overly flattened and noncircular. Often, white blood cells, specifically neutrophils, appeared damaged. For the blood film to be uniform, a large quantity of blood had to be used. Typically, the surface was flooded prior to spinning. If the entire surface was not wetted an irregular "sunburst" pattern of the blood resulted. Further, it has been found that prior art centrifuges and methods generated artifactual target cells. Target cells which are not true target cells are believed to be caused by air rushing over the slide in such a way as to roll and tumble the red cells in the blood film while the slide is spinning. This rolling and tumbling stretches the membrane of the red cell, resulting in target cells. Manual methods for obtaining a blood smear, wedge and cover-slide method, require a skilled operator, are not very reproducible, and produce distributions which are nonuniform, often containing a high percentage of damaged cells.

U.S. Pat. Nos. 3,577,267 issued to Preston et al and 3,705,048 issued to Staunton describe centrifuges which can be used to prepare blood slides but the apparatus described in these patents does not solve the problem of producing blood smears with good cell morphology, good cell distribution, and absence of artifactual target cells for all blood samples.

SUMMARY OF THE INVENTION

It is an object of the present invention to provide an economical, uniform, and reproducible means of preparing blood smeared microscope slides.

Another object of the present invention is to provide a microscope slide centrifuge which does not generate artifactual target cells and overcomes the heretofore noted disadvantages.

Briefly, according to the present invention, an apparatus for preparing blood films on a microscope slide is provided wherein the apparatus is a centrifuge including a platen suitable for accepting a microscope slide for spinning it with a flat surface thereof perpendicular to the axis of the platen. An enclosure surrounds the platen adjacent the flat microscope slide surface and parallel therewith. The enclosure is firmly attached to the platen and is spinnable therewith. These and additional objects, features and advantages of the present invention will become apparent to those skilled in the art from the following detailed description and the attached drawings, on which, by way of example, only the preferred embodiments of this invention are illustrated.

DETAILED DESCRIPTION OF THE INVENTION

It is to be noted that the drawings are illustrative and symbolic of the invention, and there is no intention to indicate scale or relative proportions of the elements shown therein.

Figure 1:
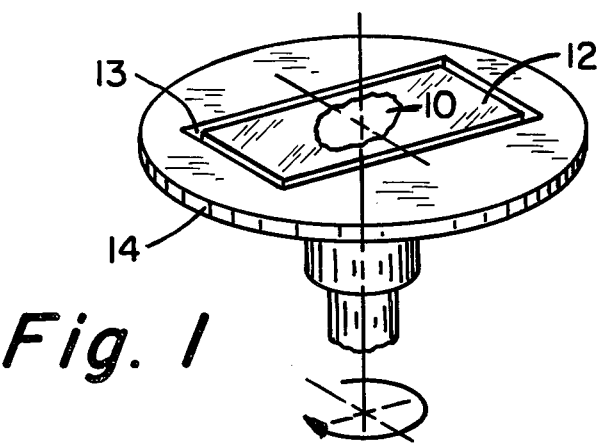
FIG. 1 is an oblique view showing a platen with a microscope slide disposed thereon.

Referring to FIG. 1, there is shown a quantity of blood 10 disposed on a microscope slide 12. Microscope slide 12 is positioned in recess 13 in platen 14. Platen 14 is affixed to the output shaft of a high torque, low inertia DC motor, not shown. Such motors are well known to one familiar with the art.

The centrifuge motor rapidly accelerates to a selected rotational velocity and is maintained at this selected velocity for a predetermined period of time.

Figure 2:
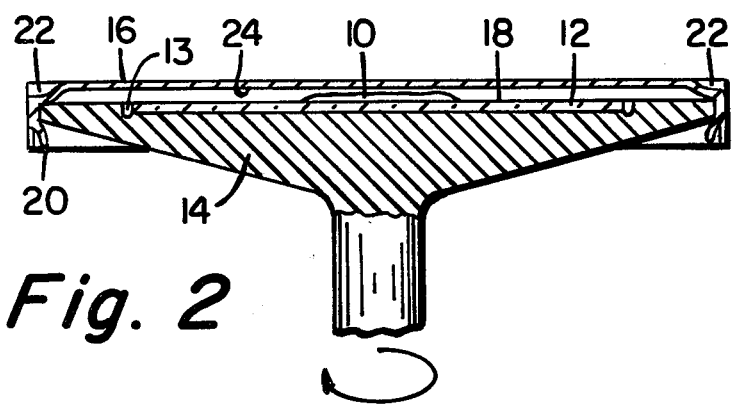
FIG. 2 is a cross-sectional view of the platen and microscope slide of FIG. 1 with a firmly attached enclosure.

Referring to FIG. 2, there is shown the platen and microscope assembly surrounded by cover or enclosure 16. Enclosure 16 is disposed adjacent the top of flat microscope slide surface 18 and parallel therewith. Enclosure 16 is firmly attached to platen 14 about the peripheral edge thereof.

Figure 3:
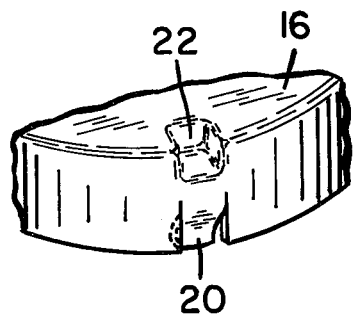
FIG. 3 is a fragmentary oblique view of the enclosure of the present invention illustrating one means for firmly attaching the enclosure to the platen.

One means of firmly attaching enclosure 18 to platen 14 is illustrated by also referring to FIG. 3. A plurality of spring clips 20 are formed about the periphery of enclosure 16 so as to clip on and rigidly hold cover 16 in place. A plurality of depressions 22 are also formed about the periphery of cover 16 to permit controlled spacing of the bottom surface 24 of enclosure 16 from surface 18 of microscope slide 12. As will be understood, the means for firmly attaching enclosure 16 to platen 14 as well as the means for maintaining the cover at a predetermined distance from the microscope slide is not critical and the means illustrated is one means by which this may be accomplished, however, any other means which will accomplish these two functions are also contemplated by the present invention.

The present invention contemplates an enclosure 16 enclosing as small a volume of air between its surface 24 and microscope slide 18 as possible to reduce the amount of air rushing into this space to the lowest possible value thereby eliminating generation of artifactual target cells created by this means. A distance between enclosure surface 24 and microscope slide surface 18 of less than 0.3 inches has been found to produce microscope slide smears of high quality. Such blood smears have been found to be uniform and reproducible.

Figure 4:
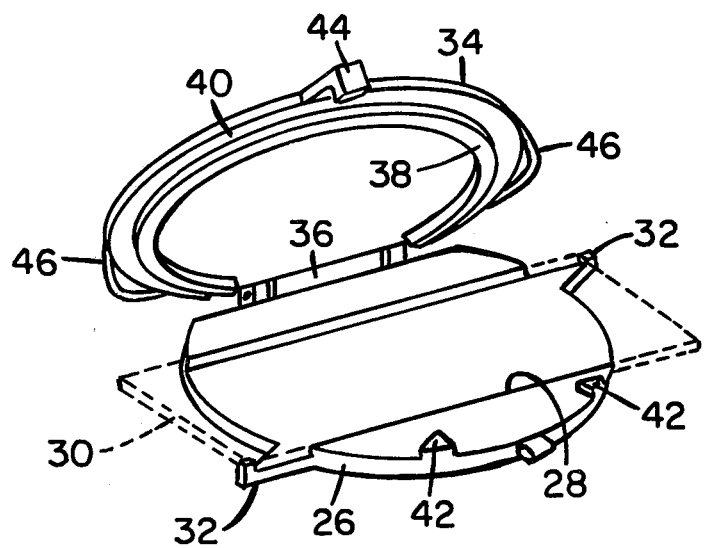
FIG. 4 is an oblique view of another embodiment of the platen and cover of the present invention.

Referring to FIG. 4, there is shown another embodiment of the present invention. A platen 26 is provided with a suitable channel 28 to receive a microscope slide 30 therein. The microscope slide extends beyond the edges of the platen, however, as will be understood, only the central portion of a microscope slide is used for examination purposes. The longitudinal position of slide 30 is maintained within the channel by means of a pair of members 32 which prohibit longitudinal movement thereof. The cover or enclosure 34 is pivotally attached to platen 26 by means of hinge 36. Cover 34 is provided with an air blockage member 38. In use, cover 34 is pivoted until surface 40 of cover 34 contacts spacer members 42 affixed to platen 26. Air blockage member 38 does not contact the microscope slide 30, rather comes into very close proximity thereto. Cover 34 is maintained in a closed relationship with platen 26 by means of latch 44, or the like. When the cover is closed, the microscope slide is held within channel 28 by means of extending springs 46 or the like, which springs 46 contact the extending portions of microscope slide 30. When the platen and cover are spun as heretofore described, the excess blood deposited on microscope slide 30 is permitted to be expelled by centrifugal force under air blockage member 38 to the exterior of the platen and cover assembly.

Figure 5:
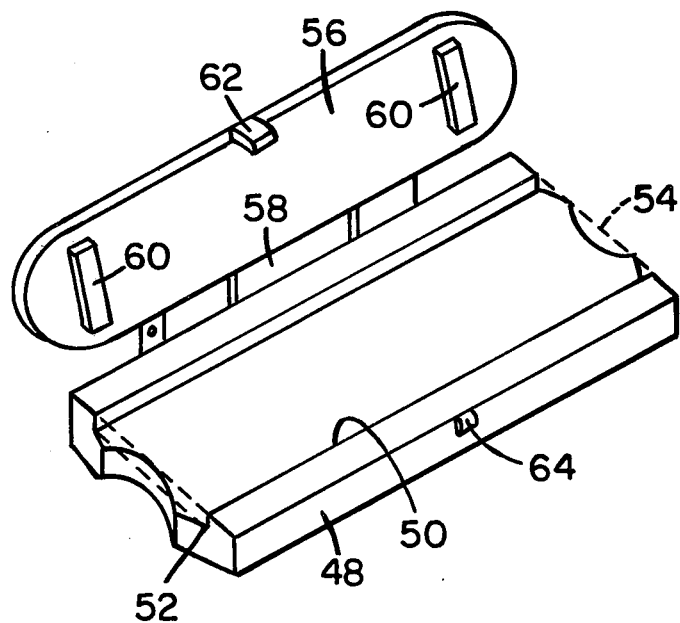
FIG. 5 is an oblique view of still another embodiment of the platen and cover of the present invention.

Referring to FIG. 5, there is shown a still further embodiment of the present invention. Platen 48 is provided with a pair of channels 50 and 52. Microscope slide 54 is fitted within inner channel 52. Enclosure or cover 56 is pivotally attached to platen 48 by means of hinge 58. At the ends of cover 56 a pair of air blockage members 60 are attached. In use, cover or enclosure 56 is pivoted until the cover is latched by means of latch members 62 and 64. The spacing between cover 56 and the top surface of microscope slide 54 may be maintained in the desired relationship by means of latch members 62 and 64 or the assembly may be provided with spacer members as heretofore described. Air blockage members 60 are loosely disposed within channel 50. When the platen and cover assembly is spun, the excess blood applied to microscope slide 54 is expelled from the assembly by means of channel 50 to the exterior thereof. As will be understood, latch members 62 and 64, as well as latch 44 of FIG. 4, may be mechanical, magnetic or other means for keeping the respective covers in the desired relationship with the respective platens.

Although the present invention has been described with respect to the specific details of certain embodiments thereof, it is not intended that such details be limitations upon the scope of the invention except insofar as set forth in the following claims.

We claim:
1. An apparatus for preparing blood films on a microscope slide comprising
a centrifuge including a platen having at least one surface suitable for accepting a microscope slide for spinning said microscope slide with a flat surface thereof perpendicular to the spin axis of the platen,
an enclosure having a broad flat interior surface closely disposed adjacent said flat microscope slide surface and parallel therewith a distance of up to about 0.3 inches, said enclosure closely surrounding said platen and substantially totally enclosing said microscope slide and said one surface of said platen,
means for firmly attaching said enclosure to said platen, and
means for spinning said platen and said enclosure together as one whereby due to said close disposition of the enclosure with respect to the microscope slide and platen, air flow between the slide and platen combination and the enclosure is minimal.
2. The apparatus of claim 1 wherein said means for firmly attaching said enclosure to said platen comprise spring clips formed at the peripheral edge of said enclosure.
3. The apparatus of claim 1 wherein said means for firmly attaching said enclosure to said platen comprise a hinge and a latch.

* * * * *